US006623502B2

(12) United States Patent
Wagner et al.

(10) Patent No.: US 6,623,502 B2
(45) Date of Patent: Sep. 23, 2003

(54) GUIDE ROD FOR TUBE SHANK INSTRUMENTS TO BE INTRODUCED INTO A BODY CAVITY

(75) Inventors: Carl Wagner, Bretten (DE); Nikolaus Beron, Bretten (DE)

(73) Assignee: Richard Wolf GmbH, Knittlingen (DE)

( * ) Notice: Subject to any disclaimer, the term of this patent is extended or adjusted under 35 U.S.C. 154(b) by 30 days.

(21) Appl. No.: 09/829,060

(22) Filed: Apr. 9, 2001

(65) Prior Publication Data

US 2001/0049533 A1 Dec. 6, 2001

(30) Foreign Application Priority Data

May 10, 2000 (DE) .......................... 100 22 861

(51) Int. Cl.[7] .............................................. A61B 17/34
(52) U.S. Cl. ...................................................... 606/185
(58) Field of Search ........................ 606/185, 191, 606/184, 198, 181, 170, 108, 167; 604/164–169, 188, 246–248, 264, 272, 274, 281, 164.01, 164.03, 164.06, 164.1, 171, 263, 160, 161, 158; 600/564

(56) References Cited

U.S. PATENT DOCUMENTS

| | | | | |
|---|---|---|---|---|
| 4,899,729 A | * | 2/1990 | Gill et al. ........................ 128/3 |
| 5,431,676 A | * | 7/1995 | Dubrul et al. .................. 606/185 |
| 5,697,946 A | * | 12/1997 | Hopper et al. ................. 606/185 |
| 5,697,947 A | * | 12/1997 | Wolf et al. ..................... 606/185 |
| 5,843,039 A | * | 12/1998 | Klemm ........................... 604/164 |
| 5,868,773 A | * | 2/1999 | Danks et al. ................... 606/185 |
| 6,036,711 A | * | 3/2000 | Mozdzierz et al. ............ 606/185 |
| 6,080,174 A | * | 6/2000 | Dubrul et al. .................. 606/185 |
| 6,162,235 A | * | 12/2000 | Vaitekunas ..................... 606/169 |
| 6,162,236 A | * | 12/2000 | Osada ............................. 606/185 |
| 6,190,360 B1 | * | 2/2001 | Iancea et al. ............... 604/164.09 |
| 6,238,407 B1 | * | 5/2001 | Wolf et al. ..................... 606/185 |
| 6,319,266 B1 | * | 11/2001 | Stellon et al. .................. 606/185 |
| 6,325,812 B1 | * | 12/2001 | Durbrul et al. ................. 606/185 |

OTHER PUBLICATIONS

Wolf Catalog (Nov. 1994) B/D/E 210.310a.

* cited by examiner

Primary Examiner—John J. Calvert
Assistant Examiner—Alissa L. Hoey
(74) Attorney, Agent, or Firm—Cohen, Pontani, Lieberman & Pavane

(57) ABSTRACT

The invention relates to a guide rod for tube shank instruments to be introduced into a body cavity which is characterised by at least two telescopic rod parts, whose ends which neighbor given the largest possible rod length, are releasably lockable with a positive or non-positive fit and whose extension movement is limited by an abutment.

9 Claims, 3 Drawing Sheets

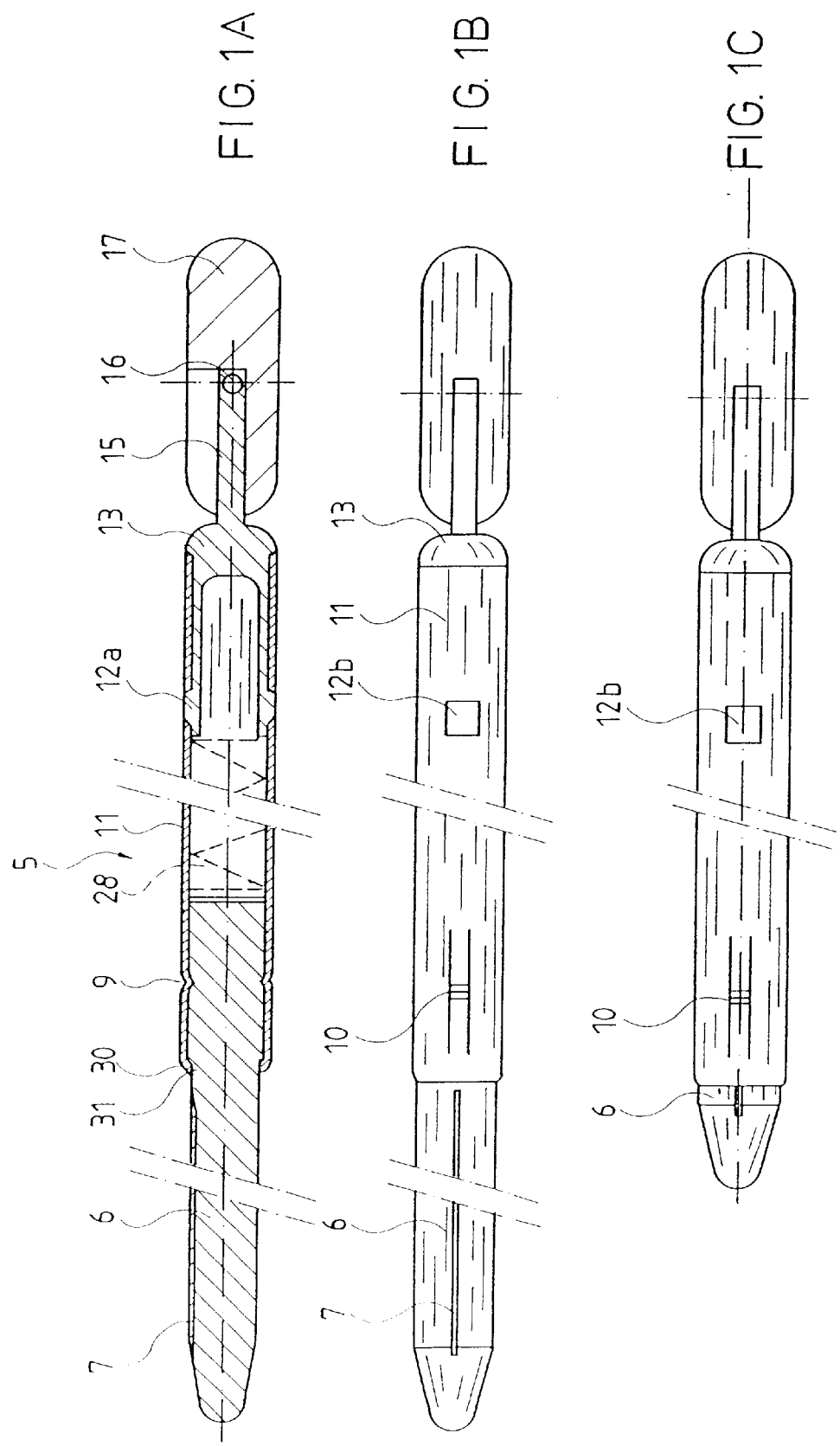

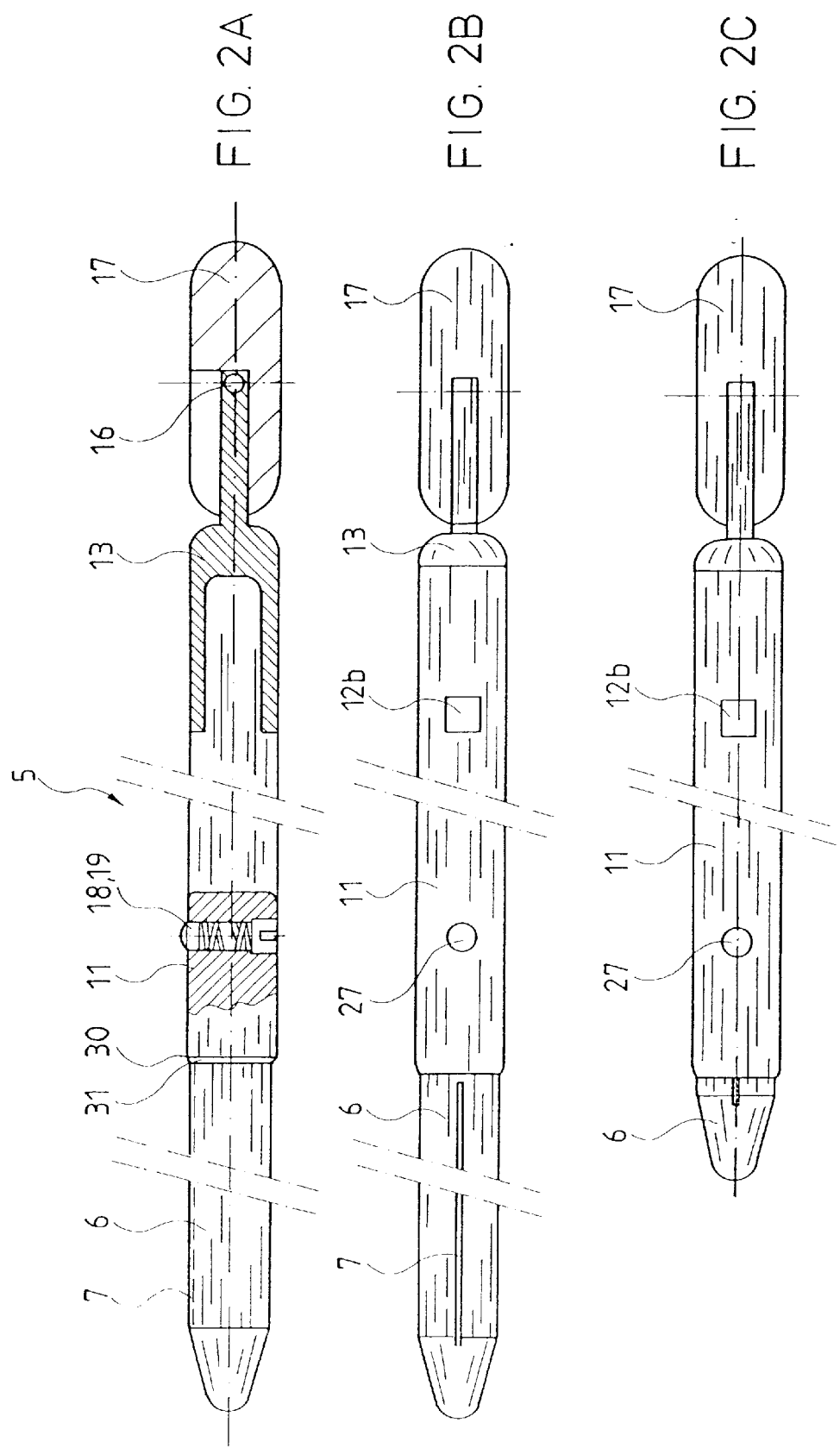

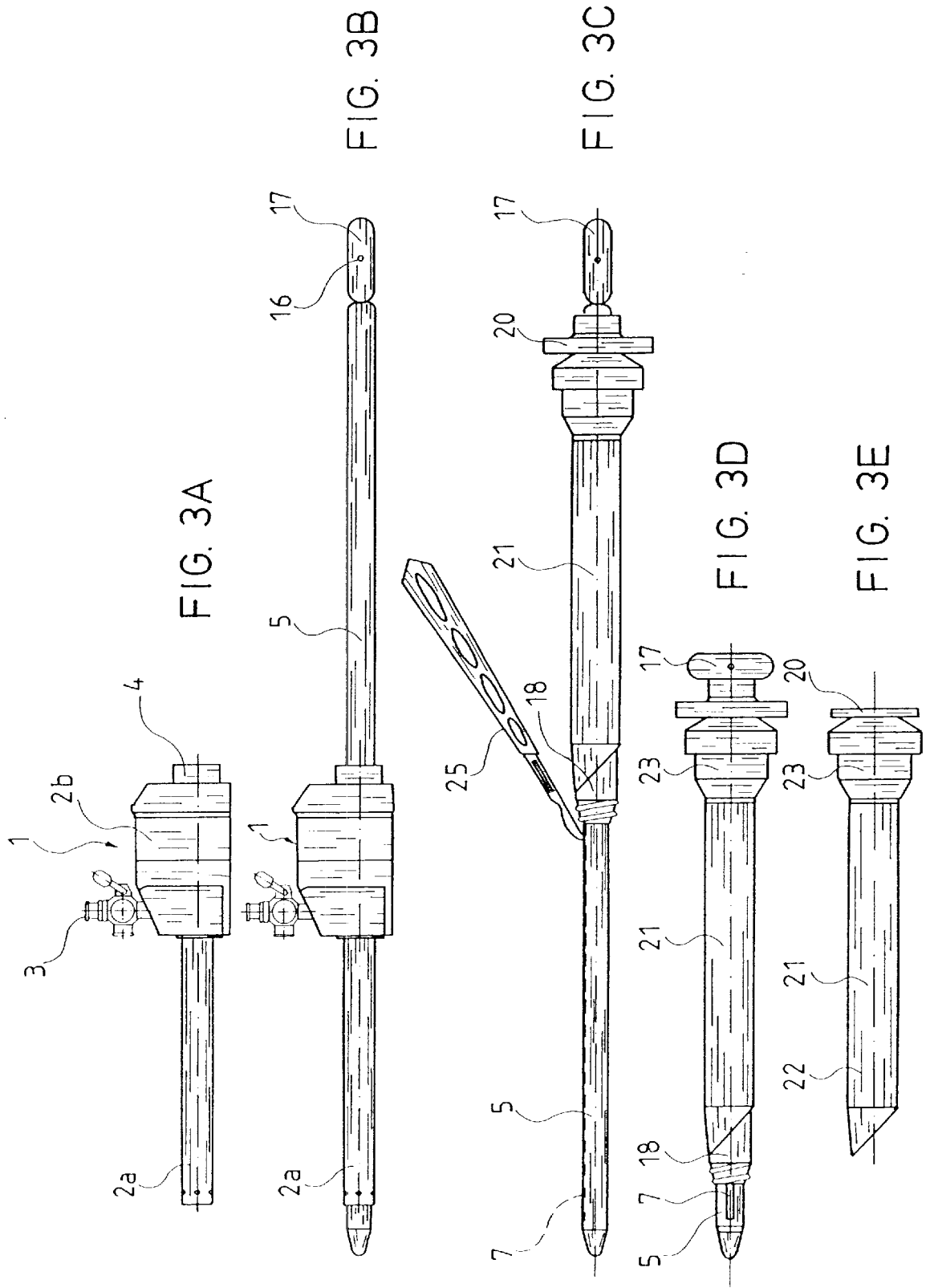

GUIDE ROD FOR TUBE SHANK INSTRUMENTS TO BE INTRODUCED INTO A BODY CAVITY

BACKGROUND OF THE INVENTION

With laprascopic operations, when for retrieving organ parts in the abdominal cavity or the application of implants a routinely used trocar sleeve is to be replaced by a trocar sleeve or working sleeve with a larger diameter, then there may result the necessity of broadening the puncture channel in the abdominal wall. This is usually carried out with a dilator. With this it is to be observed that during the sleeve change and even before the dilator is inserted, the access to the body cavity may not collapse.

Dilatation systems with a guide rod and a dilatation sleeve are known. Above all they have the shortcoming that the guide rod must be relatively long in order to be able to exchange the trocar sleeves with dilatation sleeves. On applying the trocar sleeve with larger dimensions and with a pushed-on dilatation sleeve over the guide rod, a longer guide rod however is disturbing. One must also take care with the application that the guide rod is not pushed too far distally into the abdominal cavity, since then there arises a danger of injury to the inner organs of the patient. Since a longer guide rod projects proximally quite far out of the trocar sleeve the firm gripping-round of the trocar sleeve is difficult and uncomfortable.

BRIEF SUMMARY OF THE INVENTION

It is the object of the invention to avoid the described shortcomings of existing dilatations systems and to provide a guide rod which on removal of the smaller trocar sleeve remain lying inserted and may serve as a guide when incorporating a larger trocar sleeve or working sleeve.

A guide rod achieving this object is characterised by at least two telescopic rod parts whose ends which are neighboring given the largest possible rod length are lockable and whose extension movement is limited by an abutment. The locking of the rod parts may be effected with a non-positive fit or with a positive fit.

By way of the fact that according to the invention the length of the guide rod may be telescopically changed and the rod parts displaceable to one another in the extended condition may be automatically locked or latched, an exchange of the trocar sleeves may be effected without problem and any inadvertent pushing together may be ruled out.

After pushing on the larger trocar sleeve with the dilatation sleeve, on the proximal end a grip part may be pivoted out of the guide rod axis. By way of this a falling of the guide rod into the body cavity is avoided and a firm gripping-round of the trocar sleeve is possible.

After releasing the locking of the two parts of the guide rod extended to the full length, when the distal rod end meets an organ the guide rod may thus shorten so that no excess pressure is exerted onto an organ and a danger of injury is ruled out.

By way of the fact that the guide rod can be telescoped the guide rod length in the retracted condition may be adapted to the larger trocar sleeve with the dilatation sleeve.

Since according to the invention the distal part of the guide rod at least over a section of its length is provided with a guide groove, along the guide groove in a controlled manner one may incorporate an incision extension with a standard scalpel.

The various features of novelty which characterize the invention are pointed out with particularity in the claims annexed to and forming a part of this specification. For a better understanding of the mention, its operating advantages and specific objects obtained by its use, reference should be made to the accompanying drawings and descriptive matter in which there is illustrated and described a preferred embodiment of the invention.

BRIEF DESCRIPTION OF THE DRAWINGS

FIGS. 1A to 1C a first embodiment example of a guide rod according to the invention in a longitudinal section representation and in a level plan view, in each case in the extended and retracted position, FIGS. 2A to 2C a second embodiment example of a guide rod according to the invention in each case in a partly sectioned longitudinal view and in a level plan view in each case in an extended and in a retracted condition and FIGS. 3A to 3E in each case schematically in a level plan view a trocar sleeve known from the state of the art, the guide rod inserted into the trocar sleeve, in greatest length, the whole instrument arrangement pushed onto the guide rod from the proximal side, consisting of the dilatator and of the large-lumened trocar sleeve as well as a scalpel which is guidable along the guide groove, the instrument arrangement with shortened guide rod with which the grip part comes to lie within the larger trocar sleeve, and the larger trocar sleeve per se.

DETAILED DESCRIPTION OF THE INVENTION

The guide rod 5 shown schematically in FIG. 1A consists of a distal part 6 and of a proximal tubular designed part 11 into which the proximal part 6 may be pushed in and out. A spring lock with an inwardly directed spring tongue 10 (FIG. 1B) in the region of the distal end section of the proximal rod part 11 in combination with an annular groove 9 (FIG. 1A) on the distal rod part 6 on the proximal end region of the rod part 6 ensures that with the largest possible rod length the neighboring ends of the rod part 6 and of the rod part 11 are releasably locked with a non-positive fit. Furthermore there is provided an abutment which limits the extension movement of the rod part 6 relative to the rod part 11. In this manner a securing of the distal rod part 6 is created and an inadvertent separation of the rod parts on handling the guide rod 5 is avoided. The extension movement limitation, as is evident from FIG. 1A, may be effected such that the distal end of the rod part 11 is pulled inwards (position 30 in FIG. 1A) and comes to bear on a circumferential shoulder 31 of the rod part 6 if one should attempt to pull both rod parts apart beyond the position of the previously arisen locking connection.

The distal-side rod part 6 may consist of a thick-walled tube or of a homogenous solid body, whose distal end is rounded atraumatically. The rod part 6 has a guide groove 7 running in the longitudinal direction which serves for preventing a lateral slipping of a scalpel to be advanced for widening the puncture channel from the surface of the guide rod 5.

At the proximal-side end of the rod part 11 an atraumatically formed handle part 13–17 is releasably fastened. For its releasable fastening the handle part comprises a spring clamping element 13 which is formed U-shaped on the distal-side and whose two limbs at its distal end carry radially outwardly projecting projections 12a (FIG. 1A). The rod part 11 comprises oppositely lying recesses 12b which cooperate with the two projections 12a of the spring clamping element 13 and into which the projections 12a of the spring clamping element 13 may lockingly engage. The releasability of the handle part from the proximal guide rod part 1 serves the dismantling of the guide rod into its components for an improved cleaning.

Furthermore the spring clamping element 13 has a proximally extending extension 15 on which a grip part 17 is mounted pivotably movable out of the shown position transversely to the guide rod longitudinal axis by way of a pivoting pin 16. It is to be noted that the outer diameter of the grip part 17 in its position in alignment with the guide rod longitudinal axis is not larger, but somewhat smaller than the outer diameter of the proximal rod part 11.

The second embodiment example of the guide rod 5 according to the invention shown in the FIGS. 2A to 2C for the releasable positive fit locking of the distal rod part 6 with the proximal rod part 11, instead of the spring tongue used in the embodiment example described above by way of FIGS. 1A to 1C comprises on the proximal end section of the distal rod part 6 a ball lock 19 with at least one radially movable and outwardly spring-biased locking element 18 having a spherical outer side. The proximal-side rod part 11 has in the region of its distal end a recess 27 which cooperates with the ball lock and into which the locking element 18 may lock on account of the spring bias.

All other features of this second embodiment example are identical to the features of the first embodiment example which has been described above by way of the FIGS. 1A to 1C and will not be described once again.

With the FIGS. 3A to 3E the course of an operation using the guide rod according to the invention is explained. Firstly a (non-shown) trocar with a trocar sleeve (FIG. 3A) surrounding it is introduced through a cut in the abdominal wall into the abdominal cavity. The trocar sleeve 1 shown in FIG. 3A is known from the state of the art, has a distal-side shank 2a and a valve housing 2b connecting thereto with an insufflation cock 3 and a sealing cap 4.

Then the trocar is pulled whilst the trocar sleeve 1 remains at its location. The guide rod 5 is introduced through the trocar sleeve 1 (FIG. 3B). Subsequently the trocar sleeve 1 is pulled whilst the guide rod 5 remains at its location.

Then a dilatator 18 in combination with a large-lumened trocar sleeve 21 as a unit is pressed on the guide rod 5 through the abdominal wall into the abdominal cavity. In order to limit the dilating and the subsequent introduction of the trocar sleeve to a minimum amount of time the dilatator 18 and the trocar sleeve 21 already pushed onto this are led together on the guide rod 5 firstly up to the abdominal wall. The dilating of the puncture channel is now effected in that the whole instrument arrangement consisting of the guide rod 5, the dilatator 18 and the trocar sleeve 21 is pivoted about the common longitudinal axis, with this possibly simultaneously a rotating and screwing movement is carried out and simultaneously distally introduced into the puncture channel (FIG. 3C). Should the present puncture channel not be able to be expanded to the required size then this is widened by way of a sharp-cutting scalpel blade 25. With this the mentioned guide groove 7 on the distal-side rod part 6 serves for preventing the lateral slipping of the scalpel 25 from the surface of the guide rod 5 and for leading the scalpel.

The danger that the distal end of the guide rod 5 projecting into the body cavity injures inner organs is counteracted in that the guide rod 4 after releasing the locking may be telescopically pushed together (FIG. 3D) when a correspondingly large pressure acts on the distal guide rod end coming into contact with the organ. FIG. 3D furthermore shows that the proximal-side grip part 17 may be pivoted for the secure operation and in order to prevent the guide rod sliding through the dilatation sleeve 18 into the body cavity.

FIG. 3E shows the large-lumened trocar sleeve 21 whose shank 22 on the distal side runs obliquely at an angle to the instrument longitudinal axis. At the proximal end the trocar sleeve 21 has a valve housing 23 which at the proximal-side end by be closed by way of a sealing cap 20.

Finally the dilatator 18 and the guide rod 5 are pulled whilst the trocar sleeve 21 remains in the abdominal wall and projecting into the abdominal cavity (FIG. 3E).

The non-positive fit connection of the rod parts according to FIGS. 1A to 1C is automatically lifted when the guide rod with its distal end is to meet an organ and with this a sufficiently large proximally directed pressure occurs. With the positive fit locking of the rod parts according to the FIGS. 2A to 2C the locking is released on pushing the dilatation sleeve 18 onto the guide rod (FIG. 3C) since with this the dilatation sleeve presses the outwardly projecting locking element 18 radially inwards and at least so far out of the recesss 27 that the rod parts may be pushed together.

Through the trocar sleeve 21 for example auxiliary instruments may be introduced in order to carry out operations, to remove organs or finally to introduce implants. The guide rod may also consist of more than two telescopic rod parts, wherein the pressure forces required for releasing the non-positive fit lockings of the rod parts may be set equally or having different magnitude. Furthermore a compression spring 28 acting between the rod parts may be provided which presses the distal rod part 6 distally and permits a proximal adjustment of this rod part, in the case that the guide rod with its distal end meets an organ. With a suitable design of the compression spring 28 against whose effect the rod parts may be pushed together, where appropriate also the locking means may be done away with, these locking the rod parts with one another with the largest possible guide rod length.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. A guide rod for a tube shank instrument to be introduced into a body cavity comprising:
    a rod,
        the rod having at least two telescoping rod parts having adjacent ends,
        the rod parts including
            a proximal-side rod part having a proximal end whereat there is releasably connected an atraumatically formed handle part, and
            a distal-side rod part including a longitudinal groove,
        the rod being extendable to a largest possible length, and
        the rod parts being releasably lockable; and
    whose extension movement is limited by an abutment, the abutment limiting the largest possible length of the rod.

2. A guide rod for a tube shank instrument to be introduced into a body cavity comprising:
    a rod,
        the rod having at least two telescoping rod parts having adjacent ends, the rod parts being pushed together against the effect of a spring,
the rod being extendable to a largest possible length, and
the rod parts being releasably lockable lockable; and
whose extension movement is limited by an abutment, the abutment limiting the largest possible length of the rod.

3. The guide rod of claim 1, wherein the handle part comprises a spring clamping element formed U-shaped on the distal side whose two limbs at their distal end have radially outwardly projecting projections, and the proximal rod part comprises radially opposite recesses with which the projections of the spring clamping element are lockable.

4. The guide rod of claim 3, wherein the guide rod has a longitudinal axis and the spring clamping element comprises a proximally extending extension on which a proximal grip part is pivotably movably mounted transversely to the guide rod longitudinal axis.

5. The guide rod of claim 4, wherein the proximal rod part has an outer diameter and the grip part has an outer diameter which when in alignment with the guide rod longitudinal axis is smaller than the outer diameter of the proximal rod part.

6. A guide rod for a tube shank instrument to be introduced into a body cavity comprising:
a rod,
the rod having at least two telescoping rod parts having adjacent ends,
the rod being extendable to a largest possible length, and
the rod parts being releasably lockable with a non-positive fit; and
whose extension movement is limited by an abutment, the abutment limiting the largest possible length of the rod; and
wherein for locking the rod parts
a distal-side rod part at its proximal end region comprises an annular groove, and
a proximal-side rod part in the region of its distal end comprises an inwardly directed spring tongue with a radially projecting lug.

7. A guide rod for a tube shank instrument to be introduced into a body cavity comprising:
a rod,
the rod having at least two telescoping rod parts having adjacent ends,
the rod parts including a proximal-side rod part having a proximal end whereat there is releasably connected an atraumatically formed handle part,
the rod being extendable to a largest possible length, and
the rod parts being releasably lockable with a positive fit; and
whose extension movement is limited by an abutment, the abutment limiting the largest possible length of the rod.

8. The guide rod of claim 7, wherein the least two telescopic rod parts comprise a distal-side rod part and a proximal-side having a distal end and wherein for the releasable locking of the rod parts the distal-side rod part comprises a ball lock with at least one radially moveable locking element which has a spherical outer side and which is outwardly spring-biased, the proximal-side rod part in the region of its distal end comprises a recess into which the locking element may lock.

9. The guide rod of claim 8 wherein the lock connection is releasable by way of pushing a sleeve onto the proximal-side rod part and a displacement is effected.

\* \* \* \* \*